(12) United States Patent
Bendixen et al.

(10) Patent No.: US 7,094,544 B2
(45) Date of Patent: Aug. 22, 2006

(54) GENETIC TEST FOR THE IDENTIFICATION OF CARRIERS OF COMPLEX VERTEBRAL MALFORMATIONS IN CATTLE

(75) Inventors: Christian Bendixen, Ulstrup (DK); Søren Svendsen, Randers (DK); Helle Jensen, Viborg (DK); Frank Panitz, Silkeborg (DK); Anders Aasberg, Århus N (DK); Lars-Erik Holm, Hadsten (DK); Per Horn, Viborg (DK); Anette Høj, Tjele (DK); Bo Thomsen, Århus V (DK); Mette Jeppesen, Viborg (DK); Hunnicke Vivi Nielsen, Tjele (DK); Marck Jonker, Randers (DK)

(73) Assignees: Danmarks Jordbrugsforskning, Arhus N (DK); Kvaegavlsforeningen Dansire, Randers (DK)

(*) Notice: Subject to any disclaimer, the term of this patent is extended or adjusted under 35 U.S.C. 154(b) by 21 days.

(21) Appl. No.: 10/416,941

(22) PCT Filed: Nov. 15, 2001

(86) PCT No.: PCT/DK01/00756

§ 371 (c)(1),
(2), (4) Date: Oct. 9, 2003

(87) PCT Pub. No.: WO02/40709

PCT Pub. Date: May 23, 2002

(65) Prior Publication Data

US 2004/0132032 A1    Jul. 8, 2004

(30) Foreign Application Priority Data

Nov. 16, 2000 (DK) .............................. 2000 01717
May 15, 2001 (DK) .............................. 2001 00765

(51) Int. Cl.
C07H 21/04 (2006.01)
C12Q 1/68 (2006.01)

(52) U.S. Cl. ..................... 435/6; 435/91.1; 435/91.2; 536/23.1

(58) Field of Classification Search ................... 435/6, 435/91.1, 91.2; 536/23.1, 24.3
See application file for complete search history.

(56) References Cited

U.S. PATENT DOCUMENTS 5,811,233 A    9/1998    Bowock et al.

OTHER PUBLICATIONS

Green, "DNA +EPDs=Marker-Assisted "Optimum" Selection." http://beaf-mag.com/mag/beef_dna_epds_markerassisted/, Mar. 1, 1999.*
Arriens et al. (Animal Genetics, vol. 27, pp. 429-431, 1996).*
Dequidt et al. (Vet. Immunology and Immunopathology, vol. 59, pp. 311-322, 1997).*
Hirschhorn et al. (Genetics in Medicine. vol. 4, No. 2, pp. 45-61, Mar. 2002).*
Ioannidis (Nature Genetics, vol. 29, pp. 306-309, Nov. 2001).*
Tenesa et al. (J. Anim. Sci. vol. 81, pp. 617-623, 2003).*
Schmidt et al. (J. of Interferon and Cytokine Research, vol. 22, pp. 923-934, 2002).*
Boettcher (J. Dairy Sci. vol. 87, pp. 4311-4317 2004).*
Khatib (J. Dairy Sci. vol. 88, pp. 1208-1213, 2005).*
Schnabel (PNAS, vol. 102, pp. 6896-6901, May 2005).*
Agerholm et al., 2001, *Journal of Veterinary Diagnostic Investigation*, vol. 13, pp. 283-289 Complex vertebral malformation in Holstein calves.
Barendse et al., 1997, *Mammalian Genome*, vol. 8, No. 1, pp. 21-28 A medium-density genetic linkage map of the bovine genome.
Brückner et al., 2000, *Nature* vol. 406, pp. 411-415 Glycosyltransferase activity of Fringe modulates Notch-Delta interactions.
Evrard et al., 1998, *Nature*, vol. 394, pp. 377-381 *lunatic fringe* is an essential mediator of somite segmentation and patterning.
Guillen et al., 1998, *Proceedings of the National Academy of Sciences*, vol. 95, No. 14, pp. 7888-7892 Mammalian Golgi apparatus UDP-N-acetylglucosamine transporter: Molecular cloning by phenotypic correction of a yeast mutant.
Ishida et al., 1999, *The Journal of Biochemistry*, vol. 126, No. 1, pp. 68-77 Molecular Cloning and Functional Expression of the Human Golgi UDP-N-Acetylglucosamine Transporter.
Kappes et al., 1997, *Genome Research*, vol. 7., No. 3, pp. 235-249 A Second-Generation Linkage Map of the Bovine Genome.
Klein and Arias, 1998, *Development*, vol. 125, No. 15, pp. 2951-2962 Interactions among Delta, Serrate and Fringe modulate Notch activity during *Drosophila* wing development.

(Continued)

*Primary Examiner*—Jeanine A. Goldberg
(74) *Attorney, Agent, or Firm*—Iver P. Cooper

(57) ABSTRACT

Genetic markets for identifying bovine carriers of complex vertebral malformation (CVM) disease gene are described. The genetic markers, including the microsatellite markers BM4129, INRAA003, BMS2790, ILSTS029, INRA123, BM220, HUJ246, BMS862, BMS937, BL1048, BMS2095 and BMS1266 and the bovine SLC35A3 gene, are located on bovine chromosome BTA3. The G/T polymorphism at position 559 of the bovine SLC35A3 gene is identified as being causative and diagnostic for CVM in cattle.

2 Claims, 7 Drawing Sheets

OTHER PUBLICATIONS

Figure 1:
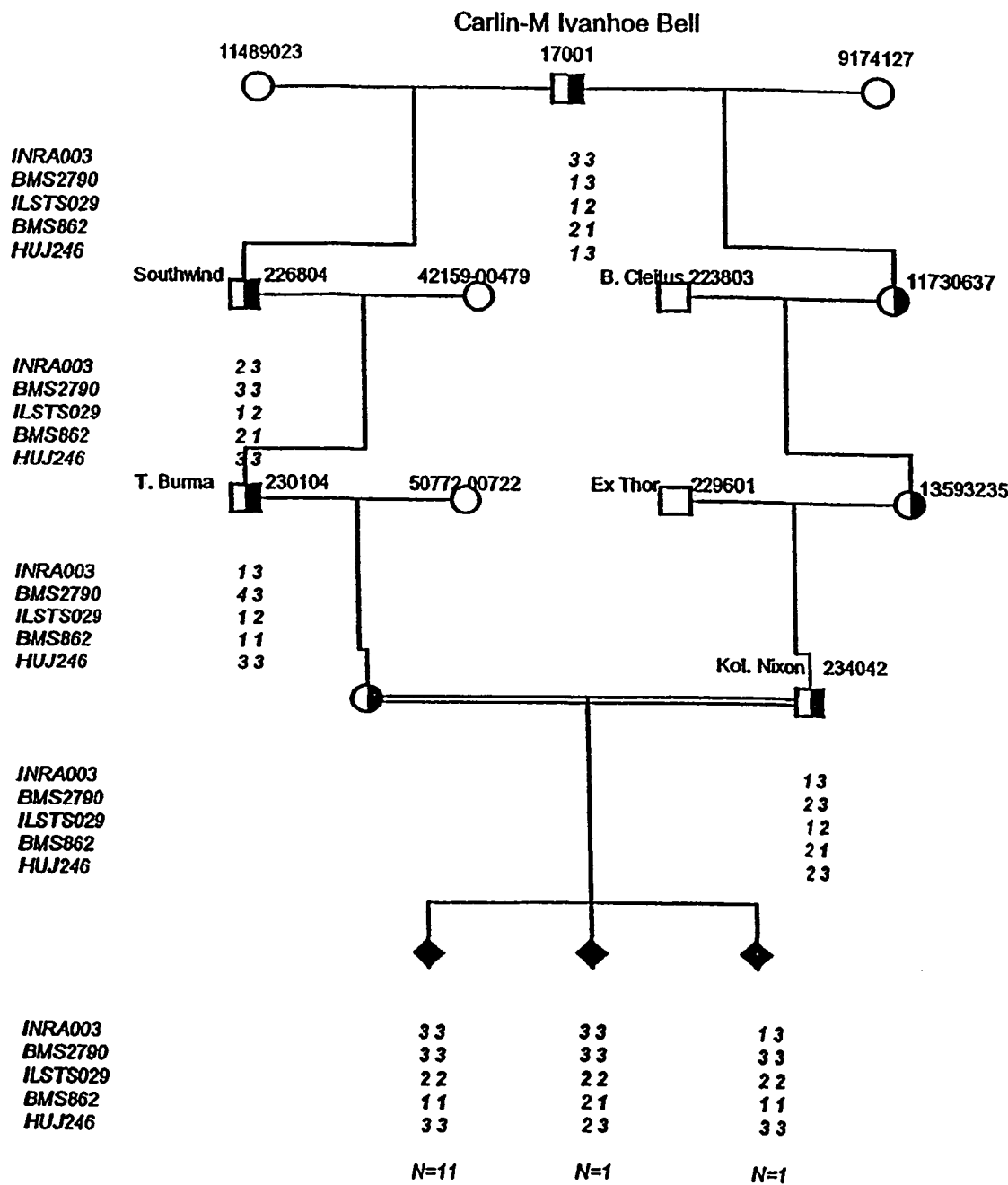

Lathrop et al., 1985, *The American Journal of Human Genetics*, vol. 37, No. 3, pp. 482-498 Multilocus Linkage Analysis in Humans: Detection of Linkage and Estimation of Recombination.

Moloney et al., 2000, *Nature,* vol. 406, pp. 369-375 Fringe is a glycosyltransferase that modifies Notch.

Solinas-Toldo et al., 1995, *Genomics,* vol. 27, No. 3, pp. 489-496 Comparative Genome Map of Human and Cattle.

Stone, R. T. et al; A Small-Insert Bovine Genome Library Highly Enriched for Microsatellite Repeat Sequences, Mammalian Genome, vol. 6, pp. 714-724 (1995).

Pinson, et al., Lecture 16 Human Genetrio III: Calculating LOD Scores, University of California Gene Tag Insertions, (Jan. 23, 2001).

Farnir, et al. "Extensive Genome-wide Linkage Disequilibrium in Cattle" Copyright 2000. Genome Research, Cold Spring Harbor Laboratory Press, ISSN 1054-9803/00 p. 220-227.

Georges, M. "Recent Progress in Livestock Genomics and Potential Impact on Breeding Programs" Copyright 2000. Theriogenology 55: p. 15-21.

\* cited by examiner

```
   1 - CAGGCAAATGAAGATAAAACAATGTCAGCCAACCTAAAATACCTTTCTTTAGGAATTTTG -   60
                       M  S  A  N  L  K  Y  L  S  L  G  I  L
  61 - GTCTTTCAGACTACCAGTTTGGTTCTGACGATGCGTTATTCTAGGACATTAAAAGAAGAG -  120
        V  F  Q  T  T  S  L  V  L  T  M  R  Y  S  R  T  L  K  E  E
 121 - GGGCCTCGTTATCTGTCATCTACAGCTGTGGTTGTTGCTGAACTTTTGAAGATAATGGCC -  180
        G  P  R  Y  L  S  S  T  A  V  V  V  A  E  L  L  K  I  M  A
 181 - TGCATTTTATTAGTCTACAAAGATAGCAAATGTAGTCTAAGAGCACTGAATCGAATACTA -  240
        C  I  L  L  V  Y  K  D  S  K  C  S  L  R  A  L  N  R  I  L
 241 - CATGATGAAATTCTTAATAAACCTATGGAAACGCTTAAACTTGCTATTCCATCAGGGATA -  300
        H  D  E  I  L  N  K  P  M  E  T  L  K  L  A  I  P  S  G  I
 301 - TATACTCTTCAGAATAATTTACTCTATGTGGCACTGTCAAATCTCGATGCAGCTACTTAT -  360
        Y  T  L  Q  N  N  L  L  Y  V  A  L  S  N  L  D  A  A  T  Y
 361 - CAGGTCACATATCAGTTGAAAATTCTTACAACTGCACTATTTTCTGTGTCAATGCTTAGT -  420
        Q  V  T  Y  Q  L  K  I  L  T  T  A  L  F  S  V  S  M  L  S
 421 - AAAAAATTAGGTGTGTACCAGTGGCTCTCCCTAGTAATTTTGATGACAGGAGTTGCTTTT -  480
        K  K  L  G  V  Y  Q  W  L  S  L  V  I  L  M  T  G  V  A  F
 481 - GTACAGTGGCCCTCAGATTCTCAAGAGCTTAATTCTAAGGAACTTTCAGCTGGCTCACAA -  540
        V  Q  W  P  S  D  S  Q  E  L  N  S  K  E  L  S  A  G  S  Q
 541 - TTTGTAGGTCTCATGGCAGTTCTACAGCATGTTTTTCCAGTGGCTTTGCTGGGGTTTAC -  600
        F  V  G  L  M  A  V  L  T  A  C  F  S  S  G  F  A  G  V  Y
 601 - TTTGAGAAAATCTTAAAAGAAACCAAACAATCAGTGTGGATAAGAAACATTCAACTTGGT -  660
        F  E  K  I  L  K  E  T  K  Q  S  V  W  I  R  N  I  Q  L  G
 661 - TTCTTTGGGAGTATATTTGGATTAATGGGTGTATATGTTTATGATGGAGAACTGGTATCA -  720
        F  F  G  S  I  F  G  L  M  G  V  Y  V  Y  D  G  E  L  V  S
 721 - AAGAATGGGTTTTTTCAGGGATATAACCGACTGACCTGGATAGTTGTTGTTCTTCAGGCA -  780
        K  N  G  F  F  Q  G  Y  N  R  L  T  W  I  V  V  V  L  Q  A
 781 - CTGGGAGGCCTTGTAATAGCTGCTGTTATTAAGTATGCGGATAACATTTTGAAAGGATTT -  840
        L  G  G  L  V  I  A  A  V  I  K  Y  A  D  N  I  L  K  G  F
 841 - GCAACCTCTTTGTCCATAATATTATCAACACTAATATCTTATTTTTGGCTACAAGATTTT -  900
        A  T  S  L  S  I  I  L  S  T  L  I  S  Y  F  W  L  Q  D  F
 901 - GTACCAACCAGTGTCTTTTTCCTTGGAGCCATCCTTGTAATAACAGCTACTTTCCTATAT -  960
        V  P  T  S  V  F  F  L  G  A  I  L  V  I  T  A  T  F  L  Y
 961 - GGTTATGATCCCAAACCTGCAGGAAATCCCACTAAAGCATAGTGGTAACTTACCTGGTTT - 1020
        G  Y  D  P  K  P  A  G  N  P  T  K  A  *
1021 - TTCACAGTGGTGCACTGGGAATCTCAACATTAATGCTGCACAGAGGACTTCTACAGATTC - 1080
1081 - TAAGAGAAAATCATCATGCTGAATCTGATCATGATGTTCAAATGGTTTGAAAATATAAAA - 1140
1141 - GTTTAAGGATAAAATATACATATATGTAACAAAATGCCTATTGCATCTAAAAATCAAAAG - 1200
1201 - TTGAACATTTCCAGGGA - 1217
```

Fig. 4

```
  1  MSANLKYLSLGILVFQTTSLVLTMRYSRTLKEEGPRYLSSTAVVVAELLKIMACILLVYK    B. Taurus
  1  .F.....V....................................................    H. Sapiens
  1  ..T.........................................................    C. Familiaris 61  DSKCSLRALNRILHDEILNKPMETLKLAIPSGIYTLQNNLLYVALSNLDAATYQVTYQLK    B. Taurus
 61  ........V...................................................    H. Sapiens
 61  ............................................................    C. Familiaris 121  ILTTALFSVSMLSKKLGVYQWLSLVILMTGVAFVQWPSDSQELNSKELSAGSQFVGLMAV    B. Taurus
121  ..........................................-.D..............    H. Sapiens
121  .............................................D.............    C. Familiaris 181  LTACFSSGFAGVYFEKILKETKQSWIRNIQLGFFGSIFGLMGVYVYDGELVSKNGFFQG    B. Taurus
180  ...................................I......................    H. Sapiens
181  ........................................I.................    C. Familiaris 241  YNRLTWIVVVLQALGGLVIAAVIKYADNILKGFATSLSIILSTLISYFWLQDFVPTSVFF    B. Taurus
240  ............I...............................................    H. Sapiens
241  ............................................................    C. Familiaris 301  LGAILVITATFLYGYDPKPAGNPTKA    B. Taurus
300  .............T...........    H. Sapiens
301  .........................    C. Familiaris
```

Fig. 5

SEQUENCE LISTING

<160> NUMBER OF SEQ ID NOS: 38

<210> SEQ ID NO 1
<211> LENGTH: 24
<212> TYPE: DNA

<213> ORGANISM: Artificial Sequence
<220> FEATURE:
<223> OTHER INFORMATION: DNA Primer

<400> SEQUENCE: 1
ctggaggtgt gtgagcccca ttta                                    24

<210> SEQ ID NO 2
<211> LENGTH: 24
<212> TYPE: DNA
<213> ORGANISM: Artificial Sequence
<220> FEATURE:
<223> OTHER INFORMATION: DNA Primer

<400> SEQUENCE: 2
ctaagagtcg aaggtgtgac tagg                                    24

<210> SEQ ID NO 3
<211> LENGTH: 20
<212> TYPE: DNA
<213> ORGANISM: Artificial Sequence
<220> FEATURE:
<223> OTHER INFORMATION: DNA Primer

<400> SEQUENCE: 3
aagacaagga ctttcagccc                                         20

<210> SEQ ID NO 4
<211> LENGTH: 22
<212> TYPE: DNA
<213> ORGANISM: Artificial Sequence
<220> FEATURE:
<223> OTHER INFORMATION: DNA Primer

<400> SEQUENCE: 4
aaagagtcgg acattactga gc                                      22

<210> SEQ ID NO 5
<211> LENGTH: 20
<212> TYPE: DNA
<213> ORGANISM: Artificial Sequence
<220> FEATURE:
<223> OTHER INFORMATION: DNA Primer

<400> SEQUENCE: 5
tgttttgatg gaacacagcc                                         20

<210> SEQ ID NO 6
<211> LENGTH: 20
<212> TYPE: DNA
<213> ORGANISM: Artificial Sequence
<220> FEATURE:
<223> OTHER INFORMATION: DNA Primer

<400> SEQUENCE: 6
tggatttaga ccagggttgg                                         20

<210> SEQ ID NO 7
<211> LENGTH: 20
<212> TYPE: DNA
<213> ORGANISM: Artificial Sequence
<220> FEATURE:
<223> OTHER INFORMATION: DNA Primer

<400> SEQUENCE: 7
tctagaggat ccccgctgac                                         20

```
<210> SEQ ID NO 8
<211> LENGTH: 20
<212> TYPE: DNA
<213> ORGANISM: Artificial Sequence
<220> FEATURE:
<223> OTHER INFORMATION: DNA Primer

<400> SEQUENCE: 8
agagagcaac tccactgtgc                                                      20

<210> SEQ ID NO 9
<211> LENGTH: 22
<212> TYPE: DNA
<213> ORGANISM: Artificial Sequence
<220> FEATURE:
<223> OTHER INFORMATION: DNA Primer

<400> SEQUENCE: 9
ttttctactg cccaacaaag tg                                                   22

<210> SEQ ID NO 10
<211> LENGTH: 22
<212> TYPE: DNA
<213> ORGANISM: Artificial Sequence
<220> FEATURE:
<223> OTHER INFORMATION: DNA Primer

<400> SEQUENCE: 10
taggtaccat agcctagcca ag                                                   22

<210> SEQ ID NO 11
<211> LENGTH: 21
<212> TYPE: DNA
<213> ORGANISM: Artificial Sequence
<220> FEATURE:
<223> OTHER INFORMATION: DNA Primer

<400> SEQUENCE: 11
actccagttt tctttcctgg g                                                    21

<210> SEQ ID NO 12
<211> LENGTH: 21
<212> TYPE: DNA
<213> ORGANISM: Artificial Sequence
<220> FEATURE:
<223> OTHER INFORMATION: DNA Primer

<400> SEQUENCE: 12
tgccatgtag tagctgtgtg c                                                    21

<210> SEQ ID NO 13
<211> LENGTH: 24
<212> TYPE: DNA
<213> ORGANISM: Artificial Sequence
<220> FEATURE:
<223> OTHER INFORMATION: DNA Primer

<400> SEQUENCE: 13
tataatgccc tctagatcca ctca                                                 24

<210> SEQ ID NO 14
<211> LENGTH: 25
<212> TYPE: DNA
<213> ORGANISM: Artificial Sequence
<220> FEATURE:
```

-continued

<223> OTHER INFORMATION: DNA Primer

<400> SEQUENCE: 14
atggaaaaat aagatgtggt atgtg                                      25

<210> SEQ ID NO 15
<211> LENGTH: 21
<212> TYPE: DNA
<213> ORGANISM: Artificial Sequence
<220> FEATURE:
<223> OTHER INFORMATION: DNA Primer

<400> SEQUENCE: 15
gtagccatgg agactggact g                                          21

<210> SEQ ID NO 16
<211> LENGTH: 21
<212> TYPE: DNA
<213> ORGANISM: Artificial Sequence
<220> FEATURE:
<223> OTHER INFORMATION: DNA Primer

<400> SEQUENCE: 16
cattatcccc tgtcacacac c                                          21

<210> SEQ ID NO 17
<211> LENGTH: 326
<212> TYPE: PRT
<213> ORGANISM: bovine SLC35A3 protein

<400> SEQUENCE: 17

Met Ser Ala Asn Leu Lys Tyr Leu Ser Leu Gly Ile Leu Val Phe Gln
1               5                   10                  15

Thr Thr Ser Leu Val Leu Thr Met Arg Tyr Ser Arg Thr Leu Lys Glu
            20                  25                  30

Glu Gly Pro Arg Tyr Leu Ser Ser Thr Ala Val Val Ala Glu Leu
        35                  40                  45

Leu Lys Ile Met Ala Cys Ile Leu Leu Val Tyr Lys Asp Ser Lys Cys
    50                  55                  60

Ser Leu Arg Ala Leu Asn Arg Ile Leu His Asp Glu Ile Leu Asn Lys
65                  70                  75                  80

Pro Met Glu Thr Leu Lys Leu Ala Ile Pro Ser Gly Ile Tyr Thr Leu
                85                  90                  95

Gln Asn Asn Leu Leu Tyr Val Ala Leu Ser Asn Leu Asp Ala Ala Thr
            100                 105                 110

Tyr Gln Val Thr Tyr Gln Leu Lys Ile Leu Thr Thr Ala Leu Phe Ser
        115                 120                 125

Val Ser Met Leu Ser Lys Lys Leu Gly Val Tyr Gln Trp Leu Ser Leu
130                 135                 140

Val Ile Leu Met Thr Gly Val Ala Phe Val Gln Trp Pro Ser Asp Ser
145                 150                 155                 160

Gln Glu Leu Asn Ser Lys Glu Leu Ser Ala Gly Ser Gln Phe Val Gly
                165                 170                 175

Leu Met Ala Val Leu Thr Ala Cys Phe Ser Ser Gly Phe Ala Gly Val
            180                 185                 190

Tyr Phe Glu Lys Ile Leu Lys Glu Thr Lys Gln Ser Val Trp Ile Arg
        195                 200                 205

Asn Ile Gln Leu Gly Phe Phe Gly Ser Ile Phe Gly Leu Met Gly Val
    210                 215                 220

-continued

Tyr Val Tyr Asp Gly Glu Leu Val Ser Lys Asn Gly Phe Phe Gln Gly
225                 230                 235                 240

Tyr Asn Arg Leu Thr Trp Ile Val Val Leu Gln Ala Leu Gly Gly
            245                 250                 255

Leu Val Ile Ala Ala Val Ile Lys Tyr Ala Asp Asn Ile Leu Lys Gly
            260                 265                 270

Phe Ala Thr Ser Leu Ser Ile Ile Leu Ser Thr Leu Ile Ser Tyr Phe
            275                 280                 285

Trp Leu Gln Asp Phe Val Pro Thr Ser Val Phe Phe Leu Gly Ala Ile
        290                 295                 300

Leu Val Ile Thr Ala Thr Phe Leu Tyr Gly Tyr Asp Pro Lys Pro Ala
305                 310                 315                 320

Gly Asn Pro Thr Lys Ala
            325

<210> SEQ ID NO 18
<211> LENGTH: 1217
<212> TYPE: DNA
<213> ORGANISM: bovine SLC35A3 cDNA

<400> SEQUENCE: 18
caggcaaatg aagataaaac aatgtcagcc aacctaaaat acctttcttt aggaattttg      60
gtctttcaga ctaccagttt ggttctgacg atgcgttatt ctaggacatt aaaagaagag     120
gggcctcgtt atctgtcatc tacagctgtg gttgttgctg aacttttgaa gataatggcc     180
tgcattttat tagtctacaa agatagcaaa tgtagtctaa gagcactgaa tcgaatacta     240
catgatgaaa tcttaataaa acctatggaa acgcttaaac ttgctattcc atcagggata     300
tatactcttc agaataattt actctatgtg gcactgtcaa atctcgatgc agctacttat     360
caggtcacat atcagttgaa aattcttaca actgcactat tttctgtgtc aatgcttagt     420
aaaaaattag gtgtgtacca gtggctctcc ctagtaattt tgatgacagg agttgctttt     480
gtacagtggc cctcagattc tcaagagctt aattctaagg aactttcagc tggctcacaa     540
tttgtaggtc tcatggcagt tctcacagca tgttttttcca gtggctttgc tggggtttac     600
tttgagaaaa tcttaaaaga aaccaaacaa tcagtgtgga taagaaacat tcaacttggt     660
ttctttggga gtatatttgg attaatgggt gtatatgttt atgatggaga actggtatca     720
aagaatgggt tttttcaggg atataaccga ctgacctgga tagttgttgt tcttcaggca     780
ctgggaggcc ttgtaatagc tgctgttatt aagtatgcgg ataacatttt gaaaggattt     840
gcaacctctt tgtccataat attatcaaca ctaatatctt attttttggct acaagatttt     900
gtaccaacca gtgtctttt cctggagcc atccttgtaa taacagctac tttcctatat      960
ggttatgatc ccaaacctgc aggaaatccc actaaagcat agtggtaact tacctggttt    1020
ttcacagtgg tgcactggga atctcaacat taatgctgca cagaggactt ctacagattc    1080
taagagaaaa tcatcatgct gaatctgatc atgatgttca aatggtttga aaatataaaa    1140
gtttaaggat aaaatataca tatatgtaac aaaatgccta ttgcatctaa aaatcaaaac    1200
ttgaacattt ccaggga                                                    1217

<210> SEQ ID NO 19
<211> LENGTH: 21
<212> TYPE: DNA
<213> ORGANISM: Artificial Sequence
<220> FEATURE:
<223> OTHER INFORMATION: DNA Primer

```
<400> SEQUENCE: 19
ggaggcaaat gaagataaaa c                                              21

<210> SEQ ID NO 20
<211> LENGTH: 18
<212> TYPE: DNA
<213> ORGANISM: Artificial Sequence
<220> FEATURE:
<223> OTHER INFORMATION: DNA Primer

<400> SEQUENCE: 20
ctatgcttta gtgggatt                                                  18

<210> SEQ ID NO 21
<211> LENGTH: 20
<212> TYPE: DNA
<213> ORGANISM: Artificial Sequence
<220> FEATURE:
<223> OTHER INFORMATION: DNA Primer

<400> SEQUENCE: 21
gagttgcttt tgtacagtgg                                                20

<210> SEQ ID NO 22
<211> LENGTH: 23
<212> TYPE: DNA
<213> ORGANISM: Artificial Sequence
<220> FEATURE:
<223> OTHER INFORMATION: DNA Primer

<400> SEQUENCE: 22
actggctact atctagcaca gga                                            23

<210> SEQ ID NO 23
<211> LENGTH: 70
<212> TYPE: DNA
<213> ORGANISM: Artificial Sequence
<220> FEATURE:
<223> OTHER INFORMATION: DNA Primer

<400> SEQUENCE: 23
cacaccgctg tacaggaaaa agtgtgccaa ccctggtcta aatccaaaat ccattatctt    60
ccaagtacat                                                           70

<210> SEQ ID NO 24
<211> LENGTH: 70
<212> TYPE: DNA
<213> ORGANISM: Artificial Sequence
<220> FEATURE:
<223> OTHER INFORMATION: DNA Primer

<400> SEQUENCE: 24
cgtcccctat gcgcttacta catacactca aatggaaatg ggaaaactgg aggtgtgtga    60
gccccattta                                                           70

<210> SEQ ID NO 25
<211> LENGTH: 20
<212> TYPE: DNA
<213> ORGANISM: Artificial Sequence
<220> FEATURE:
<223> OTHER INFORMATION: DNA Primer

<400> SEQUENCE: 25
```
aagacaagga ctttcagccc                                               20

<210> SEQ ID NO 26
<211> LENGTH: 22
<212> TYPE: DNA
<213> ORGANISM: Artificial Sequence
<220> FEATURE:
<223> OTHER INFORMATION: DNA Primer

<400> SEQUENCE: 26
aaagagtcgg acattactga gc                                            22

<210> SEQ ID NO 27
<211> LENGTH: 20
<212> TYPE: DNA
<213> ORGANISM: Artificial Sequence
<220> FEATURE:
<223> OTHER INFORMATION: DNA Primer

<400> SEQUENCE: 27
ttatacgact cactataggg                                               20

<210> SEQ ID NO 28
<211> LENGTH: 18
<212> TYPE: DNA
<213> ORGANISM: Artificial Sequence
<220> FEATURE:
<223> OTHER INFORMATION: DNA Primer

<400> SEQUENCE: 28
atttaggtga cactatag                                                 18

<210> SEQ ID NO 29
<211> LENGTH: 24
<212> TYPE: DNA
<213> ORGANISM: Artificial Sequence
<220> FEATURE:
<223> OTHER INFORMATION: DNA Primer

<400> SEQUENCE: 29
ctggaggtgt gtgagcccca ttta                                          24

<210> SEQ ID NO 30
<211> LENGTH: 24
<212> TYPE: DNA
<213> ORGANISM: Artificial Sequence
<220> FEATURE:
<223> OTHER INFORMATION: DNA Primer

<400> SEQUENCE: 30
ctaagagtcg aaggtgtgac tagg                                          24

<210> SEQ ID NO 31
<211> LENGTH: 15
<212> TYPE: DNA
<213> ORGANISM: Artificial Sequence
<220> FEATURE:
<223> OTHER INFORMATION: DNA Primer

<400> SEQUENCE: 31
ggccctcaga ttctc                                                    15

<210> SEQ ID NO 32
<211> LENGTH: 15
<212> TYPE: DNA
<213> ORGANISM: Artificial Sequence

```
<220> FEATURE:
<223> OTHER INFORMATION: DNA Primer

<400> SEQUENCE: 32
gttgaatgtt tctta                                                          15

<210> SEQ ID NO 33
<211> LENGTH: 76
<212> TYPE: DNA
<213> ORGANISM: Artificial Sequence
<220> FEATURE:
<223> OTHER INFORMATION: DNA Primer

<400> SEQUENCE: 33
cagtggccct cagattctca agagcttaat tctaaggaac tttcagctgg ctcacaattt         60
gtaggtctca tggcat                                                         76

<210> SEQ ID NO 34
<211> LENGTH: 24
<212> TYPE: DNA
<213> ORGANISM: Artificial Sequence
<220> FEATURE:
<223> OTHER INFORMATION: DNA Primer

<400> SEQUENCE: 34
cacaatttgt aggtctcatg gcag                                                24

<210> SEQ ID NO 35
<211> LENGTH: 27
<212> TYPE: DNA
<213> ORGANISM: Artificial Sequence
<220> FEATURE:
<223> OTHER INFORMATION: DNA Primer

<400> SEQUENCE: 35
gccactggaa aaacatgctg tgagaaa                                             27

<210> SEQ ID NO 36
<211> LENGTH: 139
<212> TYPE: DNA
<213> ORGANISM: Artificial Sequence
<220> FEATURE:
<223> OTHER INFORMATION: DNA Primer

<400> SEQUENCE: 36
aatgctacta ctattagtag aattgatgcc acctttcag ctcgcgcccc aaatgaaaat          60
atagctaaac aggttattga ccatttgcga aatgtatcta atggtcaaac ttttttctgg        120
aaaaacatgc tgtgagaac                                                     139

<210> SEQ ID NO 37
<211> LENGTH: 21
<212> TYPE: DNA
<213> ORGANISM: Artificial Sequence
<220> FEATURE:
<223> OTHER INFORMATION: DNA Primer

<400> SEQUENCE: 37
ggccctcaga ttctcaagag c                                                   21

<210> SEQ ID NO 38
<211> LENGTH: 23
<212> TYPE: DNA
<213> ORGANISM: Artificial Sequence
<220> FEATURE:
```

```
<223> OTHER INFORMATION: DNA Primer

<400> SEQUENCE: 38
cgatgaaaaa ggaaccaaaa ggg                                              23
```

GENETIC TEST FOR THE IDENTIFICATION OF CARRIERS OF COMPLEX VERTEBRAL MALFORMATIONS IN CATTLE

FIELD OF THE INVENTION

The present invention relates generally to a genetic disease observed in bovines termed Complex Vertebral Malformation (CVM). More particularly, the invention relates to molecular markers for identifying potential bovine carriers of CVM and for identifying the CVM gene locus and mutations thereof responsible for complex vertebral malformation in bovines.

BACKGROUND OF THE INVENTION

Complex Vertebral Malformation (CVM) is a congenital vertebral disorder detected in Holstein-Friesian (HF) black and white dairy cattle. The disease has recently been described (Agerholm et al., 2000). In Denmark, all cases diagnosed until today (Oct. 17, 2000) have been genetically related to the former elite US Holstein bull Carlin-M Ivanhoe Bell. According to the present data, CVM appears to be inherited as an autosomal recessive disease.

The disease is characterised by a congenital bilateral symmetric arthrogryposis of the distal joints and malformations of the columna, mainly at the cervico-thoracic junction combined with reduced body weight (Agerholm et al., 1994).

Externally, there are the following major findings: In many cases the cervical and/or the thoracic part of the columna seems to be short. Moderate bilateral symmetric contraction of the carpal joints and severe contraction and supination of the phalango-metacarpal joint (fetlock) are constant findings. Contraction and pronation of the phalango-metatarsal joint and slight extension of the tarsus are also common findings. In most cases an irregular course of the columna around the cervico-thoracic junction is observed. Scollosis may be observed, and lesions may be present in other regions of the columna. The irregular course is often recognised by inspection and palpation of the ventral aspect of the columna. However, lesions may be minimal and restricted to two or few vertebrae. In such cases the columna may be of almost normal length. Therefore, radiological examination of the columna is recommended to exclude vertebral malformations in suspected cases. The spinal cord is of normal size lying with the vertebral canal without obvious compressions. Using radiology, complex vertebral malformations consisting of hemivertebrae, fused and malshaped vertebrae, scollosis, and anchylosis are found at varying degrees. This is best demonstrated following removal of the arcus vertebrae. In some cases malformations of the heart are present, mostly as a high interventricular septal defect and eccentric hypertrophy of the right ventricle. Malformations of the large vessels may occur. In the lungs fetal atelectasis is present. Serohemorrhagic fluids are most present in the thoracic cavity. A variety of other malformations have been observed, but these are not constant or common findings. Lesions due to dystocia are often found.

Malformations have been observed both in aborted fetuses, prematurely born calves and in stillborn calves born at term. Cases among older calves have not yet been observed. In general the body weight is reduced, and the body weight is lower in premature born calves than in calves born at term.

Additionally, there seems to be an increased frequency of abortions in cows inseminated with semen of carrier bulls. At present the cause of this is unknown.

Presently, the only tool available for CVM diagnosis is patho-anatomical diagnosis based on the above described presence of bilateral symmetric arthrogryposis of the distal joints and malformations of the columna, mainly at the cervico-thoracic junction combined with reduced body weight. However, symmetric contractions of the limbs are common and general findings in vertebral malformations in calves. Therefore, differential diagnostic problems do exist as it is often difficult to differentiate between CVM and other malformations.

The fact that the genetic defect appears to be spread by the bull Carlin-M Ivanhoe Bell which has been used intensively all over the world makes it of significant economic importance to be able to test whether current and potential breeding bulls are carriers of the defect.

In order to obtain an estimate of the frequency of potential CVM carrier animals within the Danish cattle population, the present inventors have extracted pedigree information from the Danish national cattle database. At the time of the extraction (October 2000) there were registered 919,916 pure-bred cows and heifers, and 169,821 pure-bred bulls and male calves. Bell was found 707,915 times in the pedigrees of the cows and heifers and 161,043 times in the male pedigrees. In Tables 1 and 2 below, the number of occurrences of Bell in each generation of the pedigrees is shown.

TABLE 1

Occurrence of Bell in the pedigrees of Danish Holstein cows and heifers

| Generations NR | Frequency | Percent | Cumulative Frequency |
|---|---|---|---|
| 2 | 21240 | 3.0 | 21244 |
| 3 | 202460 | 28.6 | 223704 |
| 4 | 321043 | 45.4 | 544747 |
| 5 | 133956 | 18.9 | 678703 |
| 6 | 27307 | 3.9 | 706010 |
| 7 | 1869 | 0.3 | 707879 |
| 8 | 36 | 0.0 | 707915 |

TABLE 2

Occurrence of Bell in the pedigrees of Danish Holstein bulls

| Generation | Frequency | Percent | Cumulative Frequency |
|---|---|---|---|
| 2 | 436 | 0.3 | 436 |
| 3 | 20144 | 12.5 | 20580 |
| 4 | 82394 | 51.2 | 102974 |
| 5 | 44545 | 27.7 | 147519 |
| 6 | 12455 | 7.7 | 159974 |
| 7 | 1040 | 0.6 | 161014 |
| 8 | 29 | 0.0 | 161043 |

Although these numbers also include some double and triple occurrences of Bell in the pedigrees, the data dearly show that a majority of the Danish Holstein cattle are potential carriers of CVM. Clearly, the problem is immense on a global scale.

Thus, there is great demand in the cattle industry for a genetic test that permits the identification of cattle in various breeds that are potential carriers of CVM (e.g. before detectable onset of clinical symptoms).

Prior to the present invention, microsatellite mapping has not been applied to the gene causing the above complex vertebral malformations which has not been isolated or characterised. Thus, to the inventors' best knowledge, the diagnostic method according to the invention described in further detail in the following has not previously been suggested or disclosed.

Accordingly, the present invention, which comprises mapping of the disease locus for CVM, has provided a DNA test based on microsatellite markers located on bovine chromosome BTA3. The ability of the test to define the carrier status of animals descending from Bell has been confirmed which appears from the examples below.

SUMMARY OF THE INVENTION

In its broadest aspect, the present invention provides a method for detecting the presence in a bovine subject of a genetic marker associated with bovine complex vertebral malformation (CVM), comprising the steps of providing a bovine genetic material, and detecting in the genetic material the presence or absence of at least one genetic marker that is linked to a bovine complex vertebral malformation disease trait or a specific nucleotide polymorphism which causes the complex vertebral malformation disease trait.

In a further aspect, the invention pertains to a diagnostic kit for use in detecting the presence in a bovine subject of at least one genetic marker associated with bovine complex vertebral malformation (CVM), comprising at least one oligonucleotide sequence selected from the group consisting of SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO: 33, SEQ ID NO: 34, SEQ ID NO: 35, SEQ ID NO: 36, SEQ ID NO: 37 and SEQ ID NO: 38, and combinations thereof. Furthermore, the invention relates to a diagnostic method including a diagnostic kit for the detection of a G/T polymorphism in the bovine SLC35A3 gene causative and diagnostic for CVM in cattle.

DETAILED DISCLOSURE OF THE INVENTION

One primary objective of the present invention is to enable the identification of cattle carrying bovine complex vertebral malformation (CVM). This is achieved by a method which detects the presence of a genetic marker associated with bovine CMV in a bovine subject. More specifically, the genetic marker may be the bovine SLC35A3 gene or even more specifically specific polymorphisms in the bovine SLC35A3 gene.

As used herein, the term a "bovine subject" refers to cattle of any breed. Thus, any of the various cow or ox species, whether male or female, are included in the term, and both adult and new-born animals are intended to be covered. The term does not denote a particular age. One example of a bovine subject is a member of the Holstein-Friesian cattle population.

The term "genetic marker" refers to a variable nucleotide sequence (polymorphic) that is present in bovine genomic DNA on a chromosome and which is identifiable with specific oligonucleotides. Such a variable nucleotide sequence is e.g. distinguishable by nucleic acid amplification and observation of a difference in size or sequence of nucleotides due to the polymorphism. In useful embodiments, such genetic markers may be identified by several techniques known to those skilled in the art, and include typing of microsatellites or short tandem repeats (STR), restriction fragment length polymorphisms (RFLP), detection of deletion or insertion sites, and random amplified polymorphic DNA (RAPD) as well as the typing of single nucleotide polymorphism (SNP) by methods including restriction-fragment-length polymerase chain reaction, allele-specific oligomer hybridisation, oligomer-specific ligation assays, mini-sequencing, direct sequencing, fluorescence-detected 5'-exonuclease assays, and hybridisation with PNA and LNA probes and others. However, it will be appreciated that other genetic markers and techniques may be applied in accordance with the invention.

As described above, "bovine complex vertebral malformations" (CVM) is a congenital vertebral disorder. Presently, the disease has only been detected in Holstein-Friesian (HF) black and white dairy cattle; however, it is also contemplated that other bovine races may be affected. The disease has recently been described by Agerholm et al., 2000. Accordingly, in the present context CVM and bovine complex vertebral malformation disease trait are to be understood as a disease resulting in the clinical symptoms previously described herein, and as reported and defined by Agerholm et al., 2000.

The method according to the invention includes the provision of a bovine genetic material. Such material include bovine DNA material which may be provided by any conventional method or means. The bovine DNA material may e.g. be extracted, isolated and purified from blood (e.g., fresh or frozen), tissue samples (e.g., spleen, buccal smears), hair samples containing follicular cells and semen.

As previously described, the method of the present invention further comprises a step of detecting in the genetic material the presence or absence of a genetic marker that is linked to a bovine complex vertebral malformation disease trait.

In order to detect if the genetic marker is present in the genetic material, standard methods well known to persons skilled in the art may be applied, e.g. by the use of nucleic acid amplification. In order to determine if the genetic marker is genetically linked to the complex vertebral malformation disease trait, a lod score can be applied. A lod score, which is also sometimes referred to as $Z_{max}$, indicates the probability (the logarithm of the ratio of the likelihood) that a genetic marker locus and a specific gene locus are linked at a particular distance. Lod scores may e.g. be calculated by applying a computer programme such as the MLINK programme of the LINKAGE package (Lathrop et al., 1985). A lod score of greater than 3.0 is considered to be significant evidence for linkage between the genetic marker and the complex vertebral malformation disease trait or gene locus.

Figure 2:
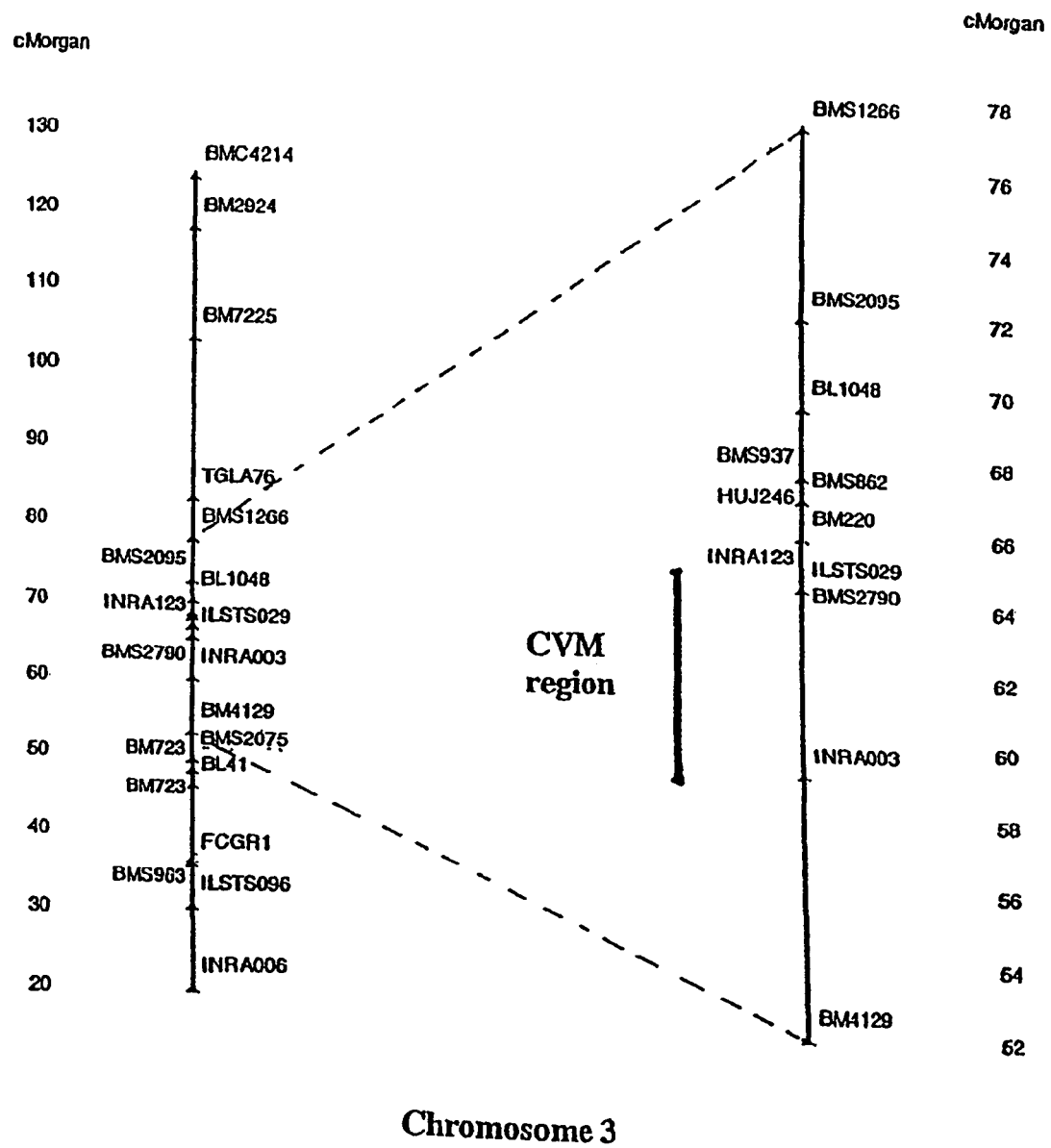

In one embodiment of the invention, the genetic marker is located on bovine chromosome BTA3. The region of bovine chromosome BTA3 comprising the genetic markers that are useful in the method of the present invention is indicated in FIG. 2.

Accordingly, genetic markers located on bovine chromosome BTA3 in the region flanked by and including the polymorphic microsatellite markers BM4129 and BMS1266, may be useful according to the present invention. In one specific embodiment, the at least one genetic marker is located in the region from about 59.5 cM to about 67.9 cM on bovine chromosome BTA3.

In a further useful embodiment, the at least one genetic marker is located on the bovine chromosome BTA3 in the region flanked by and including the polymorphic microsatellite markers INRAA003 and BMS937.

In a further aspect, the at least one genetic marker is located on the bovine chromosome BTA3 in the region flanked by and including the polymorphic microsatellite markers INRAA003 and ILSTS029.

In another advantageous embodiment, the at least one genetic marker is selected from the group consisting of microsatellite markers BM4129, INRAA003, BMS2790, ILSTS029, INRA123, BM220, HUJ246, BMS862, BMS937, BL1048, BMS2095 and BMS1266.

As described in the examples, the at least one genetic marker may be linked to a gene causing the bovine complex vertebral malformation disease. Thus, in one embodiment, the at least one genetic marker is located on bovine chromosome BTA3 in the region flanked by and including the polymorphic microsatellite markers BM4129 and BMS1266 and genetically linked to the CVM disease trait or the CVM gene locus at a lod score of at least 3.0, such as at least 4.0, including at least 5.0, such as at least 6.0, including at least 7.0 such as at least 8.0, including at least 9.0 such as at least 10.0, including at least 11.0, such as at least 12.0.

The specific definition and locus of the above polymorphic microsatellite markers can be found in the USDA genetic map (Kappes et al., 1997).

It will be appreciated that in order to detect the presence or absence in a bovine subject of a genetic marker associated with CVM, more than one genetic marker may be applied in accordance with the invention. Thus, the at least one marker can be a combination of two or more genetic markers which are shown to be informative whereby the accuracy of the test can be increased.

Accordingly, as further exemplified below, in one useful embodiment, two or more of the microsatellite markers INRAA003, BMS2790, ILSTS029, INRA 123, BM220, HUJ246, BMS862, BMS937 can be used in combination.

In accordance with the invention, the nucleotide sequences of the primer pairs for amplifying the above microsatellite markers are described in Table 4 below.

The comparative maps (Solinas-Toldo et al., 1995) show that most of bovine chromosome BTA3 corresponds to a part of human chromosome 1 (HSA1). The genetic mapping of the CVM locus presented herein makes it possible to use the information available about human genes and to concentrate the search for the candidate gene to genes present on human chromosome 1. This will greatly limit the number of candidate genes and facilitate the search for the CVM causative gene.

Genetic markers of the present invention can be made using different methodologies known to those skilled in the art. Thus, it will be understood that with the knowledge presented herein, the nucleotide sequences of the above described polymorphic microsatellite markers of bovine chromosome BTA3 have been identified as being genetically linked to the CVM gene locus, and additional markers may be generated from the known sequences or the indicated location on bovine chromosome BTA3 for use in the method of the present invention.

For example, using the map illustrated in FIG. 2, the CVM region of bovine chromosome BTA3 may be microdissected, and fragments cloned into vectors to isolate DNA segments which can be tested for linkage with the CVM gene locus. Alternatively, with the nucleotide sequences provided in Table 4, isolated DNA segments can be obtained from the CVM region by nucleic add amplification (e.g., polymerase chain reaction) or by nucleotide sequencing of the relevant region of bovine chromosome BTA3 ("chromosome walking").

Additionally, the above described homology between bovine chromosome BTA3 and human chromosome 1 (HSA1) indicates that any gene or expressed sequence tag that is mapped to this analogous region in human may also map to the CVM region of bovine chromosome BTA3. Thus, genes or conserved sequences that map on human chromosome HSA1 may be analysed for linkage to the CVM gene locus using routine methods.

Genotyping is based on the analysis of genomic DNA which can be provided by using standard DNA extraction methods as described herein. When the genomic DNA is isolated and purified, nucleic add amplification (e.g. polymerase chain reaction) can be used to amplify the region of the DNA corresponding to each genetic marker to be used in the analysis for detecting the presence in a bovine subject of a genetic marker associated with CVM. Accordingly, a diagnostic kit for use in such an embodiment comprises, in a separate packing, at least one oligonucleotide sequence selected from the group consisting of SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO: 33, SEQ ID NO: 34, SEQ ID NO: 35, SEQ ID NO: 36, SEQ ID NO: 37 and SEQ ID NO: 38, and combinations thereof.

Identification of a Mutation in the Bovine SLC35A3 Gene Causative and Diagnostic for CVM in Cattle Having established the genomic localisation of the CVM gene delimited by polymorphic microsatellite markers, a search for the identification of the structural gene and the causative mutation herein was performed which can be used as an ultimate genetic marker for CMV.

The human genome sharing sequence homology to the CVM region, defined as the region between the markers INRA003 and ILSTS029, was identified. The marker BMS2790 is located in this interval (FIG. 1). Initially, 5 different clones from a bovine BAC library (RPCI-42, constructed and made available by P. de Jonge and co-workers) were identified, each harbouring one of the markers INRA003, ISLTS029, or BMS2790. Using sequence information obtained from these BAC clones, a single region on human chromosome 1 which contained a region of homology to the marker-containing BACs was identified using the BLASTN programme on public sequence databases. This region spans about 6 million base pairs and is located in position approx. 107.4–113.5 (FIG. 3) (ENSEMBL viewer, The Sanger Centre).

Isolation and Sequencing of the SLC35A3 cDNA

Based on a homology alignment of the SLC35A3 gene between homo sapiens and canis familiaris, 2 oligos (SL1F and SL8R) were designed for amplification of almost the entire cDNA for bovine SLC35A3, including the start codon. PCR was performed on cDNA isolated from heart tissue samples collected from a wildtype animal, a CVM carrier, and an affected animal, respectively. To obtain the sequence of the 3'-end of the gene, the resulting PCR fragment was sequenced and a new oligo designed (SL5F). To amplify the 3' end of SLC35A3, SL5F was used in combination with an oligo (bSLCBVIR), designed using the published sequence of a partial bovine EST (genbank, dbEST). The cDNA sequence (SEQ ID NO: 18) and the translated peptide sequence (SEQ ID NO: 17) of bovine SLC35A3 is shown in FIG. 4. The protein encoded by bovine SLC35A3 contains 326 amino acids and shares homology to a family of previously known proteins involved in the transport of nucleotide sugars from the cytosol into the Golgi lumen. The alignment depicted in FIG. 5 shows the homology to SLC35A3 proteins previously described in human (Ishida et al. 1999) and in dog (Guillen et al. 1998).

Detection of a Polymorphism in the SLC35A3 Gene

To detect potential polymorphisms in the bovine SLC35A3 gene, PCR amplification of the gene was performed using cDNA isolated from heart tissue samples collected from a CVM carrier and an affected animal, respectively. Sequencing of the fragment isolated from the affected animal revealed a sequence identical to the wildtype, except for the affected animal being homozygous for the nucleotide T in nucleotide position 559, compared to the wildtype animal being homozygous for G in the corresponding position (see FIG. 4). Sequencing of the cDNA from an animal being carrier of the CVM-defect showed this animal to be heterozygous having both T and G in position 559.

The exchange of G to T in position 559 affects the sequence of the resulting peptide in changing a valine in position 180 to a phenylalanine (see FIG. 4).

Typing the SLC35A3 Polymorphism by a DNA Sequencing Based Assay

Figure 6:
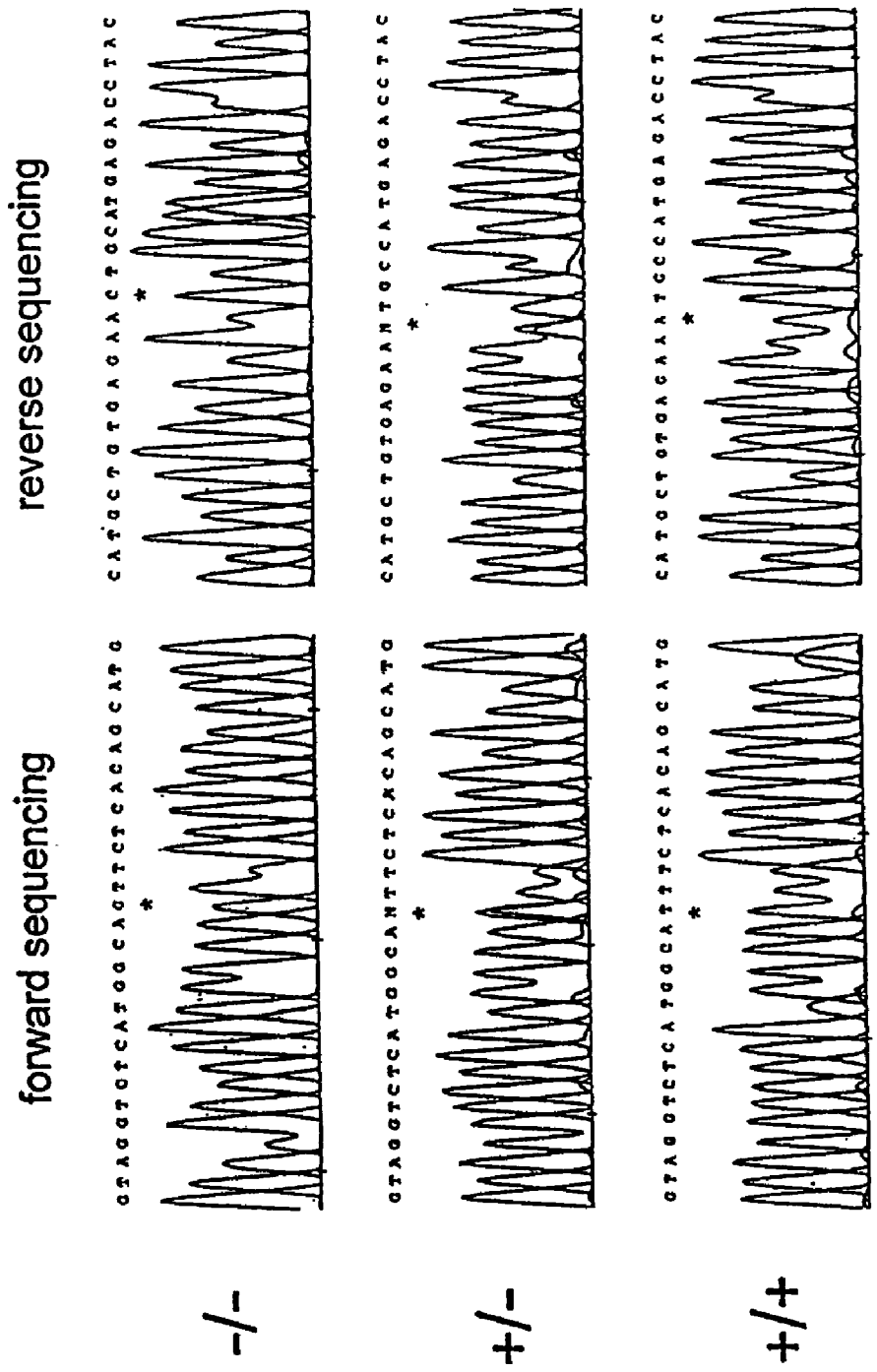

FIG. 6 shows the results obtained from sequencing a PCR fragment amplified from genomic DNA and containing the region (from 544 to 572 of the SLC35A3 cDNA, for numbering see FIG. 4) containing the G/T mutation. The left and right panels show forward and reverse sequencing, respectively. The upper row (marked by −/−) shows the wildtype result, showing a G in the polymorphic position using forward sequencing and a C in the similar position on the other strand using reverse sequencing (marked by asterisks). The lower row +/+ shows the results from an affected calf, showing a T in the polymorphic position using forward sequencing and an A in the similar position on the other strand using reverse sequencing (marked by asterisks). The heterozygote (+/−) is shown in the middle panel and expectedly displays as a mixture of the wildtype and affected signal and thus has both a T and a G signal using forward sequencing and an A and a C signal on the other strand.

All Calves Affected by CVM are Homozygous for the T-allele

Genotyping of 39 calves affected by CVM was performed by sequencing of a PCR product amplified from genomic DNA (see FIG. 6 and example 6). All of these animals were homozygous for the T-allele, confirming the initial results.

The T-allele is not Found in Animals Unrelated to Bell

Since calves affected by CVM have been reported only in pedigrees containing the widely used bull BELL, it was investigated whether the T-allele was present in animals unrelated to BELL. Taking advantage of the Danish Cattle Database, 496 animals of the Holstein breed without BELL in their pedigree were identified and sampled. Genotyping of these animals was performed by sequencing of a PCR product amplified from genomic DNA (see FIG. 6 and example 6). None of these animals contained the T-allele, suggesting that this allele is found exclusively in the line of animals closely related to BELL.

By sequencing, more than 326 unrelated (at least for the last three generations) animals of 12 different breed were also genotyped. All of these animals were homozygous for the wildtype allele (G-allele) again demonstrating the lack of the CVM-related allele (the T-allele) in the general cattle population.

Typing the SLC35A3 Polymorphism by an Allele-specific PCR Assay (AS-PCR)

Figure 7:
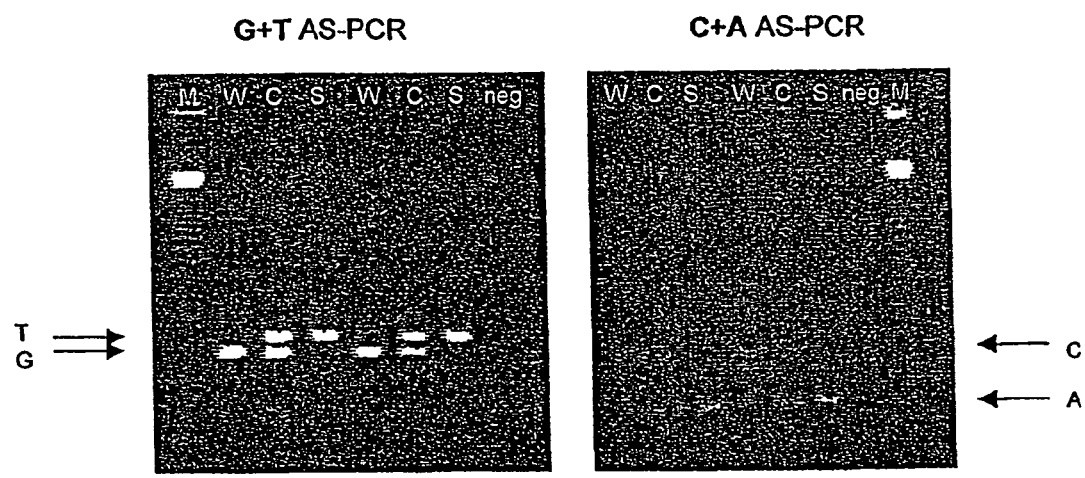

In order to type the G/T polymorphism efficiently, an allele-specific PCR assay using BIOLASE Diamond DNA Polymerase from Bioline was developed. This polymerase requires a perfect match of the 3' end of the primer to the template, and a mismatch at this position will result in no (or very weak) amplification. In this way, it is possible to distinguish between wildtype, carrier or sick animals by identifying the presence or absence of allele-specific PCR products (FIG. 7). The left part of FIG. 7 shows the Allele-Specific PCR products of the coding strand. As expected, wild type animals show amplification with the G-specific primer but not with the T-specific primer. The carriers show amplification of both the G- and T-specific primers, while sick animals only show amplification of the T-specific primer. The right part shows the Allele-Specific PCR products of the non-coding strand, and as expected, the patterns are the same as the coding strand. Wild type animals are homozygotic C, carriers are heterozygotic C/A, and sick animals are homozygotic A.

From the above described results of using a positional candidate gene approach, a bovine gene was identified which is homologous to the human gene SLC35A3 encoding a UDP-N-acetylglucosamine transporter. Within this gene a G/T polymorphism was identified which alters the amino acid sequence of the protein. All affected calves analysed

(39) are homozygous for the T-allele (T/T) and known carriers (108) are all heterozygous for the polymorphism (G/T). Analysis of more than 500 animals of the Holstein breed, chosen as being unrelated to Bell, failed to identify any animals carrying the T-allele. More than 1500 animals were analysed having Bell in the pedigree without finding any unaffected animal being homozygous for the T-allele. Furthermore, more than 300 cattle selected from 12 different breeds were analysed without detecting the T-allele in any of these animals. Taken together, the findings described in the present application demonstrate that the T-allele is present in a single copy in animals which are carriers of CVM and in two copies in animals affected by CVM. Detection of the T-allele in position 559 (numbering from FIG. 4) is therefore diagnostic for CVM and ideal for detection of carriers of the CVM defect.

As the G/T polymorphism has been identified as being causative for CMV, any genetic markers closely coupled to this polymorphism may be diagnostic for CMV in a bovine population. Accordingly, the present invention describes a method to identify bovine subjects either affected by CMV or carriers of CMV by determining the presence of the G/T polymorphism at position 559 of the bovine SLC35A3 gene, either indirectly by analysing any genetic markers, such as microsatellites described herein, coupled to the bovine SLC35A3 gene or directly by analysing the sequence of the bovine SLC35A3 gene, e.g. as described above and in further details in the examples.

Within the scope of the present invention is therefore a method for detecting and/or quantifying the presence of a genetic marker associated with bovine CVM in a bovine subject in order to be able to identify the CMV affected bovine subjects or carriers of CMV. The steps of the method comprises:
a) providing a bovine genetic material, and
b) detecting, in said genetic material, the presence or absence of at least one genetic marker that is linked to a bovine complex vertebral malformation disease trait.

The at least one genetic marker is linked to a gene causing bovine CMV disease, said gene being identified herein to be the bovine SLC35A3 gene which encodes the bovine SLC35A3 protein comprising an amino acid sequence as shown in SEQ ID NO: 17.

More specifically, the present invention relates to a method for detecting bovine CMV, wherein the genetic marker is a single nucleotide polymorphism at a position equivalent to nucleotide 559 of SEQ ID NO:18, said single nucleotide polymorphism being a G/T polymorphism.

The present application furthermore describes an efficient assay for the genotyping of the present polymorphism using allele-specific PCR. This is but one of a battery of methods for the typing of SNPs, other methods which could be employed include, but are not limited to, mini-sequencing, primer-extension, pyro-sequencing, PCR-RFLP, allele-specific rolling circle-amplification, primer-extension followed by MALDI-TOF mass-spectrometry as well as a range of other enzymatic and hybridisation-based methods.

A phenotype resembling CVM has been demonstrated to exist in mice mutated in the gene lunatic fringe (Evrad et al., 1998). Similar to calves affected by CVM, mice homozygous for a null mutation in lunatic fringe exhibit an altered somite segmentation and patterning, having a shortened body axis, vertebral- and rib-fusions and incompletely formed vertebrae (Evrad et al., 1998). Fringe seems to participate in the definition of boundary formation and somite patterning by modulating the activity of notch receptors (Klein and Arias, 1998; Moloney et al., 2000, Brückner et al., 2000). The Notch-modulating activity seems to be mediated by an N-acetylglucosaminyl-transferase activity of Fringe, which in Golgi initiates the elongation of O-linked fucose residues attached to EGF-like sequence repeats of Notch (Moloney et al., 2000; Brückner et al., 2000).

Furthermore, as the bovine SLC35A3 gene is homologous to the human SLC35A3 gene, it is, with the information given herein, obvious to analyse the coding sequence of the human SLC35A3 gene for causative and diagnostic mutations when studying human developmental defects, especially involving somite-segmentation and patterning.

The effect of a mutation in the Golgi-located N-acetylglucosaminyl transporter (SLC35A3) affecting transport of N-acetylglucosamine from the cytosol into the lumen of Golgi would be expected to deprive the Fringe family of proteins for their substrate. This would affect the ability of Fringe to modulate Notch activity and thereby cause a segmentation defect like CVM. It therefore seems very plausible that the mutation in SLC35A3, apart from being diagnostic for CVM, is also the mutation causing this widespread genetic defect.

The invention is described in further details in the following examples:

EXAMPLES

Example 1

Genetic Mapping of Complex Vertebral Malformation (CVM)

This example illustrates the localisation of the CVM gene locus to bovine chromosome BTA3. Additionally, this embodiment describes the identification of markers linked to the CVM gene locus, and thus the characterisation of the CVM region of bovine chromosome BTA3.

In order to map the locus responsible for CVM, samples were obtained from animals participating in a breeding study. Briefly, approx. 300 cows and heifers descending from the bull T Burma and inseminated with semen from the bull KOL Nixon were selected for the breeding study. Thirteen affected calves were selected on the basis of the post mortem examination, as described in Agerholm et al., 2000. These 13 calves as well as their parents, in total 28 animals, were used in the initial genome scan. The calves were separated by 4 generations to their common ancestor, the purebred bull Carlin-M Ivanhoe Bell.

The genome scan was conducted, covering all 29 autosomes, using a battery of micro-satellite markers picked from the USDA genome map (Kappes et al., 1997). Markers were selected with pair-wise distances between 10 and 20 cM. In areas of doubt due to low marker informativity, new markers were included and typed. A total of 194 markers were used. PCR reactions were performed in duplexes in a volume of 5 µl in an ABI 877 PCR robot (Applied Biosystems), containing 12 ng of genomic DNA, 1×PCR buffer, 0.4

U AmpliTaq Gold (Applied Biosystems), 20 mmol of each primer and 2.0 mM MgCl$_2$. All markers were run at the same touchdown PCR conditions: Incubation at 94° C. for 12 minutes to activate the enzyme, 35 cycles at 94° C., 30 sec; Ta, 45 sec; 72° C., 20 sec, ending with a final extension at 72° C. for 10 min. The first ten cycles Ta decreased from 67° C. to 58° C., one degree for each cycle, and the remaining 25 cycles Ta were fixed at 58° C. PCR products were pooled and 5 to 9 different markers were run in each lane on an ABI 377 (Applied Biosystems), and gels were analysed with the accompanying software. Alleles were assigned with the Genotyper programme (Version 2.1, Applied Biosystems).

For three markers, two-point lod scores were calculated using the MLINK programme of the LINKAGE package (Lathrop et al., 1985). Due to the pedigree structure (FIG. 1) with multiple inbreeding loops, the pedigree was divided into thirteen small families, one for each affected calf including the Sire (KOL Nixon), the dam and the maternal grandsire (T Burma). The disease was assumed to be recessively inherited with a complete penetrance of the genotype.

Significant linkage was found for all three markers. The highest lod score (Z) was observed with BMS2790 and ILSTS029 with Z=10.35 at θ=0. Furthermore, the nearby marker INRA003 was also significantly linked to the CVM locus (Table 3).

TABLE 3

Two point lod scores (Z) and recombination fractions (θ) from the linkage analysis of the CVM locus and bovine chromosome 3 markers.

| Marker | Recombination fraction (θ) | Lod score (Z) |
|---|---|---|
| BMS2790 | 0.00 | 10.35 |
| INRA003 | 0.03 | 6.44 |
| ILSTS029 | 0.00 | 10.35 |

The above results locate the CVM locus to BTA3 (FIG. 2) according to the USDA genetic map (Kappes et al., 1997).

Eleven calves were homozygous for the interval defined by INRA003, BMS2790, ILSTS029, BMS862 and HUJ246, while BMS2790 and ILSTS029 alone were homozygous in all thirteen calves as depicted in FIG. 1. It was possible to construct haplotypes of these markers, allowing us to deduce the most likely CVM haplotype (FIG. 1). The haplotypes are defined by the size of the marker alleles which are numbered from 1 to N where 1 defines the shortest allele of the amplified marker and N defines the longest allele. The actual length of the alleles associated with CVM in Bell is as follows:

INRA003 (allele no. 3): 176 base pairs
BMS2790 (allele no. 3): 118 base pairs
ILSTS029 (allele no. 2): 164 base pairs
BMS862 (allele no. 1): 130 base pairs
HUJ246 (allele no. 3): 262 base pairs The actual length of the alleles will depend upon the primers used to amplify the marker, and the fragment lengths shown above is based on using the primers described in Table 4.

Furthermore, seventeen additional affected calves sampled as part of the Danish surveillance programme for genetic defects were included in the study. All affected animals had the pure-bred bull Bell as a common ancestor. DNA was extracted from blood samples or semen using standard procedures.

The 17 calves and their mothers were genotyped with the 8 markers INRA003, BMS2790, ILSTS029, BM220, INRA123, BMS862, BMS937, and HUJ246 spanning the region on BTA3 from approximately 59.5 cM to 67.9 cM, and since the CVM gene in the additional 17 calves, like in the initial breeding study, was assumed to originate from the common ancestor bull Bell, a similar region of identity by descent (IBD) was expected to exist in all affected calves. This also turned out to be the case: in 17 out of 17 calves the chromosome segment defined by INRA003 and BMS2790 was homozygous, sharing the same alleles as the animals from the breeding study. In two of the nineteen animals, heterozygosity was observed in the ILSTS029 and BMS862 locus explained by single recombination events between BMS2790 and ILSTS029. Thus, based on the combined genotyping results, we have found that the CVM genetic defect is most likely located in an interval of less than 6 cM, flanked by the markers INRA003 and ILSTS029 as illustrated in FIG. 2 and denoted "CVM region".

The sequences of the primers for the applied 8 markers INRA003, BMS2790, ILSTS029, BM220, INRA123, BMS862, BMS937, and HUJ246, are depicted in Table 4 below.

TABLE 4

| Genetic marker | Sequence of primers | SEQ ID NO |
|---|---|---|
| INRA003 | F: CTG GAG GTG TGT GAG CCC CAT TTA | SEQ ID NO: 1 |
|  | R: CTA AGA GTC GAA GGT GTG ACT AGG | SEQ ID NO: 2 |
| BMS2790 | F: AAG ACA AGG ACT TTC AGC CC | SEQ ID NO: 3 |
|  | R: AAA GAG TCG GAC ATT ACT GAG C | SEQ ID NO: 4 |
| ILSTS029 | F: TGT TTT GAT GGA ACA CAG CC | SEQ ID NO: 5 |
|  | R: TGG ATT TAG ACC AGG GTT GG | SEQ ID NO: 6 |
| INRA123 | F: TCT AGA GGA TCC CCG CTG AC | SEQ ID NO: 7 |
|  | R: AGA GAG CAA CTC CAC TGT GC | SEQ ID NO: 8 |
| BM220 | F: TTT TCT ACT GCC CAA CAA AGT G | SEQ ID NO: 9 |
|  | R: TAG GTA CCA TAG CCT AGC CAA G | SEQ ID NO: 10 |
| HUJ246 | F: ACT CCA GTT TTC TTT CCT GGG | SEQ ID NO: 11 |
|  | R: TGC CAT GTA GTA GCT GTG TGC | SEQ ID NO: 12 |

TABLE 4-continued

| Genetic marker | Sequence of primers | SEQ ID NO |
|---|---|---|
| BMS862 | F: TAT AAT GCC CTC TAG ATC CAC TCA | SEQ ID NO: 13 |
| | R: ATG GAA AAA TAA GAT GTG GTA TGT | SEQ ID NO: 14 |
| BMS937 | G F: GTA GCC ATG GAG ACT GGA CTG | SEQ ID NO: 15 |
| | R: CAT TAT CCC CTG TCA CAC ACC | SEQ ID NO: 16 |

Example 2

Diagnostic Test to Identify CVM Carriers:

A diagnostic test to determine bovine carriers of CVM was established by determining whether descendants from Bell were carriers of the disease-associated haplotype.

The test was based upon the 8 microsatellite markers INRA003, BMS2790, ILSTS029, BM220, INRA123, BMS862, BMS937 and HUJ246, and relied upon the recognition of the disease specific alleles or haplotype (see FIG. 1) in animals descending from Bell.

Animals were thus determined to be carriers if they had inherited the disease-associated alleles in the region defined by the markers INRA003, BMS2790, ILSTS029, and BM220 from Bell or from animals descending from Bell. If the animals had not inherited the disease-associated haplotype from Bell or from animals descending from Bell, they were determined to be non-carriers. In cases where the Bell haplotype had been split by recombination, the animals were designated as indeterminable. The four additional markers were only used when the information content in the test markers was decreased due to inability to distinguish between maternal and paternal inheritance.

Like all diagnostic genetic tests based upon linked DNA markers, the CVM test suffers from the drawback that a double recombination event (one event at each side of the causative gene, between the gene and the flanking markers) cannot be detected. In the present case, this event will be extremely rare due to the tight linkage between the markers and the CVM gene, and the reliability of the test is estimated to be higher than 99%.

Example 3

Tissue Dissection and RNA Isolation and cDNA Synthesis:

Roughly 5 grams of heart tissue were dissected from dead-born calves within 3 hours of delivery, immediately frozen in liquid nitrogen and stored at −80° C. 250 mg of tissue was used for RNA isolation. RNA was isolated using the RNA Isolation Kit from Stratagene (cat. 200345).

cDNA was synthesised by mixing 2.5 μg of total RNA with 1 μl of oligo $(dT)_{12-18}$ (500 μg/ml), 1 μl of 10 mM dNTP mix and $H_2O$ to give a final volume of 12 μl. The resulting mixture was heated at 65° C. for 5 min, chilled on ice and spun briefly. Following the addition of 4 μl of 5× first-strand buffer, 2 μl of 0.1 M DTT and 1 μl of $H_2O$, the contents were mixed and incubated at 42° C. for 2 min, after which 1 μl (200 U) of Superscript II (GibcoBRL® Lifetechnologies) was added and the incubation allowed to continue at 42° C. for 1.5 hours. The reaction was inactivated at 70° C. for 15 min. To remove RNA, the cDNA was incubated at 37° C. for 20 min with 1 U RNase H (Roche Molecular Biochemicals).

Example 4

Sequencing of SLC35A3:

Based on a homology alignment of the SLC35A3 gene between homo sapiens and canis familiaris, 2 oligos (SL1F and SL8R) were designed for amplification of almost the entire cDNA for bovine SLC35A3, including the start codon. To obtain the 3' end of the gene, the resulting PCR fragment was sequenced and a new oligo designed (SL5F). To amplify the 3' end of SLC35A3, SL5F was used in combination with an oligo (bSLCBVIR), based on a published sequence of a bovine EST.

The same PCR conditions were applied for both primer sets.

The PCR reactions were performed in a GeneAmp® PCR System 9700 (Applied Biosystems) in a final volume of 10 μl consisting of 1 μl of 10×$NH_4$ reaction buffer, 0.5 μl of 50 mM $MgCl_2$, 0.8 μl of dNTPs (2.5 mM of each), 5.65 μl $H_2O$, 1 μl of forward and reverse primer (5 pmol of each) and 0.05 μl of 5 U/μl BIOTAQ DNA polymerase (Bioline).

The touchdown PCR reaction consisted of an initial heat activation step at 95° C. for 2 min followed by 10 cycles of denaturation for 30 sec at 95° C., annealing at 62° C. for 30 sec (0.5° C. decrements), and elongation for 20 sec at 72° C., plus an additional 30 cycles with a denaturation step for 30 sec at 95° C., an annealing temperature of 57° C. for 30 sec and an elongation step at 72° C. for 30 sec.

The following primers were used to amplify the complete SLC35A3 cDNA:

```
SL1F:     5'-GGA GGC AAA TGA AGA TAA AAC-3'    (SEQ ID NO: 19)

SL8R:     5'-CTA TGC TTT AGT GGG ATT3-'        (SEQ ID NO: 20)

SL5F:     5'-GAG TTG CTT TTG TAC AGT GG-3'     (SEQ ID NO: 21)

bSLCBVIR: 5'-ACT GGC TAC TAT CTA GCA CAG GA-3' (SEQ ID NO: 22)
```

The complete cDNA sequence was obtained by applying these primers in four separate cycle sequencing reactions using purified PCR products as the template. The PCR products were purified using SPIN-X® (Corning Incorporated) from a 0.8% Seakem agarose gel.

Cycle sequencing reactions were carried out in a GeneAmp® PCR System 9700 (Applied Biosystems) and included an initial step at 96° C. for 2 min followed by 99 cycles of 96° C. for 10 sec, 55° C. for 5 sec and 60° C. for 4 min. Sequencing products were precipitated with two volumes of ethanol and ⅒ volume of 3 M NaAc (pH 5.5), PCR Screening of the Bovine BAC Library:

BAC pools were prepared from the BAC library and screened by PCR. The PCR reactions were performed in a GeneAmp® PCR System 9700 (Applied Biosystems) in a final volume of 10 μl consisting of 1 μl of 10×NH$_4$ reaction buffer, 0.5 μl of 50 mM MgCl$_2$, 0.8 μl of dNTPs (2.5 mM of each), 5.65 μl of H$_2$O, 1 μl of forward and reverse primer (5 pmol of each) and 0.05 μl of 5 U/μl BIOTAQ DNA polymerase (Bioline).

The following primers were used to identify BMS2790 containing BAC clones by PCR:

```
BMS2790F: 5'-AAG ACA AGG ACT TTC AGC CC-3'    (SEQ ID NO: 25)

BMS2790R: 5'-AAA GAG TCG GAC ATT ACT GAG C-3' (SEQ ID NO: 26)
``` washed with 70% ethanol, resuspended in 5 μl of loading buffer and run on 4% acrylamide sequencing gels using an ABI377 automatic sequencer.

The cDNA sequence of the bovine SLC35A3 is shown in FIG. 4 (SEQ ID NO: 18).

Example 5

Identification and Isolation of BACs Containing Microsatellite Markers

Filter Hybridisation:

The filters were pre-hybridised in hybridisation solution (6×SSC (52.6 g of NaCl, 26.46 g of sodium citrate per liter), 5× Denhardt (2 g of ficoll (type 400, Pharmacia), 5 g of polyvinylpyrrolidone, 5 g of bovine serum albumin (Fraction V, Sigma), 0.5% SDS and 50 μg/ml SS-DNA) at 65° C. for 3 hours with rotation. 100 μl of 5'-end labelled oligonucleotide was then incubated with the filters for 16 hours at 65° C. For end labelling, 5 pmol of oligonucleotide was combined with 5 μl (50 μCi) of gamma-$^{32}$P-ATP (specific activity>5000 Ci/mmole), 2 μl of 10× kinase buffer, 11 μl of H$_2$O and 1 μl (10 U) of T4 polynucleotide kinase (New England Biolabs Inc.), and the mix was incubated at 37° C. for 1.5 hours followed by 5 min of boiling to heat inactivate the enzyme. The labelled probe was NaAc/ethanol precipitated using standard procedures, and after a wash in 70% ethanol, the probe was redissolved in 100 μl of H$_2$O. Following hybridisation the filters were washed once with wash solution I (2×SSC, 0.2% SDS) and twice at 65° C. with wash solution II (0.1×SSC, 0.5% SDS), and exposed to Kodak BIOMAX™ MS film for 2 days at −80° C.

The following 5'-end labelled oligonucleotides were used to identify ILSTS029 and INRA003 positive BAC dones:

The touchdown PCR reaction consisted of an initial heat activation step at 95° C. for 2 min followed by 10 cycles of denaturation for 30 sec at 95° C., annealing at 70° C. for 30 sec (0.5° C. decrements), and elongation for 20 sec at 72° C., plus an additional 30 cycles with a denaturation step at 95° C. for 30 sec, annealing at 65° C. for 30 sec and elongation at 72° C. for 20 sec.

BAC DNA Isolation and Sequencing:

BAC DNA was prepared according to Qiagens Large Construct Kit, and approximately 1 μg of BAC DNA was used as the template for cycle sequencing performed with the BigDye™ Terminator Cycle Sequencing Kit (PE Applied Biosystems). The cycle sequencing reactions were performed in a final volume of 6 μl containing 1 μl of Big Dye™ Terminator mix, 1 μl of primer (5 pmol), 1 μl of reaction buffer and 2 μl of H$_2$O. Cycle sequencing reactions were carried out in a GeneAmp® PCR System 9700 (Applied Biosystems) and included an initial step at 96° C. for 2 min followed by 130 cycles of 96° C. for 10 sec, 55° C. for 5 sec and 60° C. for 4 min. Sequencing products were precipitated with two volumes of ethanol and ⅒ volume of 3 M NaAc (pH 5.5), washed with 70% ethanol, resuspended in 2 μl of loading buffer and run on 4% acrylamide sequencing gels using an ABI377 automatic sequencer.

```
ILSTS029 oligo: 5'-CAC ACC GCT GTA CAG GAA AAA GTG TGC CAA CCC TGG TCT AAA   (SEQ ID NO: 23)
                TCC AAA ATC CAT TAT CTT CCA AGT ACA T-3'

INRA003 oligo:  5'-CGT CCC CTA TGC GCT TAC TAC ATA CAC TCA AAT GGA AAT GGG   (SEQ ID NO: 24)
                AAA ACT GGA GGT GTG TGA GCC CCA TTT A-3'
```

Sequencing Primers:

```
T7:         5'-TTA TAC GAC TCA CTA TAG GG-3'        (SEQ ID NO: 27)

SP6:        5'-ATT TAG GTG ACA CTA TAG-3'           (SEQ ID NO: 28)

INRA003F:   5'-CTG GAG GTG TGT GAG CCC CAT TTA-3'   (SEQ ID NO: 29)

INRA003R:   5'-CTA AGA GTC GAA GGT GTG ACT AGG-3'   (SEQ ID NO: 30)
```

Example 6

Determination of CVM Status by Sequencing:

PCR reactions (2 µl of purified template/sample genomic DNA, 2 µl of 10×PCR buffer, 2 µl of 25 mM MgCl$_2$, 3.3 µl of 0.2 mM of each dNTP (Ultrapure dNTP, 27-2033-01; Amersham Pharmacia Biotech), 6 pmol of primer (forward: CBFEX1, 5'-GGC CCT CAG ATT CTC-3' (SEQ ID NO: 31); reverse: CBTEXR, 5'-GTT GAA TGT TTC TTA-3') (SEQ ID NO: 32), 0.165 U Taq polymerase (Biotaq, M95801B; Bioline), dH$_2$O ad total volume) were performed oil-free in 96-well plates using a Primus HT (MWG Biotech AG). Cycling conditions: 95° C. 120 sec, 35×[95° C. 60 sec, 60° C. 30 sec, 72° C. 110 sec]. Post-reaction clean-up was done by gel filtration (Millipore Filtration System) with Sephadex G-50 Superfine (17-0041-01, Amersham Pharmacia Biotech) carried out according to the manufacturer's recommendation, using 50 µl of dH$_2$O for final sample elution. Forward and reverse sequencing reactions were performed with the same primers as used for the generation of the PCR product (2 µl of PCR product, 8 µl of Sequencing Mix, 0.6 µl of 6 pmol Primer (see above), dH$_2$O ad 20 µl; DYEnamic ET Dye Terminator Cycle Sequencing Kit (US81095). After thermocycling (30×[95° C. 20 sec, 55° C. 15 sec, 60° C. 70 sec]) samples were cleaned by gel filtration essentially as described above and analysed on a MegaBACE1000 (Amersham Pharmacia Biotech) using LPA long-read matrix and the following sequencing conditions: 90 sec injection at 3 kV and 35 min run time at 9 kV.

Example 7

Allele-specific PCR Assay:

Primers were designed from the cDNA sequence and the four allele-specific primers were designed to have the 3' base at the position of the mutation.

Primer sequences:

```
T_fwd:        5'-CAG TGG CCC TCA GAT TCT CAA GAG CTT AAT TCT AAG GAA CTT TCA    (SEQ ID
                                                                                NO: 33)
              GCT GGC TCA CAA TTT GTA GGT CTC ATG GCA T-3'

G_fwd:        5'-CAC AAT TTG TAG GTC TCA TGG CAG-3'                             (SEQ ID
                                                                                NO: 34)

A_rev:        5'-GCC ACT GGA AAA ACA TGC TGT GAG AAA-3'                         (SEQ ID
                                                                                NO: 35)

C_rev_link*:  5'-aat gct act act att agt aga att gat gcc acc ttt tca gct cgc gcc cca aat  (SEQ ID
                                                                                NO: 36)
              gaa aat ata gct aaa cag gtt att gac cat ttg cga aat gta tct aat ggt caa act ttt ttC TGG AAA AAC ATG CTG TGA GAA C-3'

Fwd:          5'-GGC CCT CAG ATT CTC AAG AGC-3'                                 (SEQ ID
                                                                                NO: 37)

Rev:          5'-CGA TGA AAA AGG AAC CAA AAG GG-3'                              (SEQ ID
                                                                                NO: 38)
```

The C_rev_link primer contains a linker sequence from the M13 phage (shown in lower case letters). This linker was added to obtain a longer PCR product in order to be able to multiplex the C- and A-primers in one PCR reaction. The 3' base at the position of the mutation is shown in bold. The C- and G-primers are specific for the wildtype allele, while the T- and A-specific primers are specific for the mutation.

Primer pairs:
C- and A-specific multiplex: Fwd+A_rev+C_rev_link (lower strand)
T-specific reaction: T_fwd+Rev (upper strand)
G-specific reaction: G_fwd+Rev (upper strand)

AS-PCR Conditions:

Each PCR reaction was carried out in a 10 µl volume containing 20–100 ng of genomic DNA, 0.025 units/µl of BIOLASE Diamond DNA polymerase, 0.75 mM dNTPs, 3 mM MgCl$_2$, 0.25 pmol/µl primer (0.125 pmol/µl of the two reverse primers in the multiplex) in 1×NH4 buffer (Bioline). PCR was carried out in a GeneAmp® PCR System 9700 (PE Applied Biosystems) under the following conditions: 95° C. for 4 min, 35 cycles of 94° C. for 30 s, 62° C. (56° C. for the T- and G-reaction) at ramp 80% for 30 s, and 72° C. for 30 s followed by a final extension at 72° C. for 7 min and storage at 4° C. PCR was followed by electrophoresis in a 2% agarose gel at 200 V for 30 min.

The results of the allele-specific PCR analysis of two wildtype, two carriers, and two sick animals are shown in FIG. 7.

Figure Legends

FIG. 1 shows the pedigree used to locate the bovine complex vertebral malformation (CVM) locus and haplotypes of five microsatellite markers on bovine chromosome 3. The most likely CVM haplotypes are in bold. Filled black squares represent affected calves. Double lines between the sire and the dams indicate inbreeding loop. N refers to the number of animals. Genotypes of the thirteen different dams are for simplicity reasons not shown.

FIG. 2 shows the genetic map of bovine chromosome 3. Numbers on the sides refer to the genetic distances given in centiMorgan (cM) along the chromosome. The most likely location of the bovine complex vertebral malformation (CVM) locus is indicated.

Figure 3:
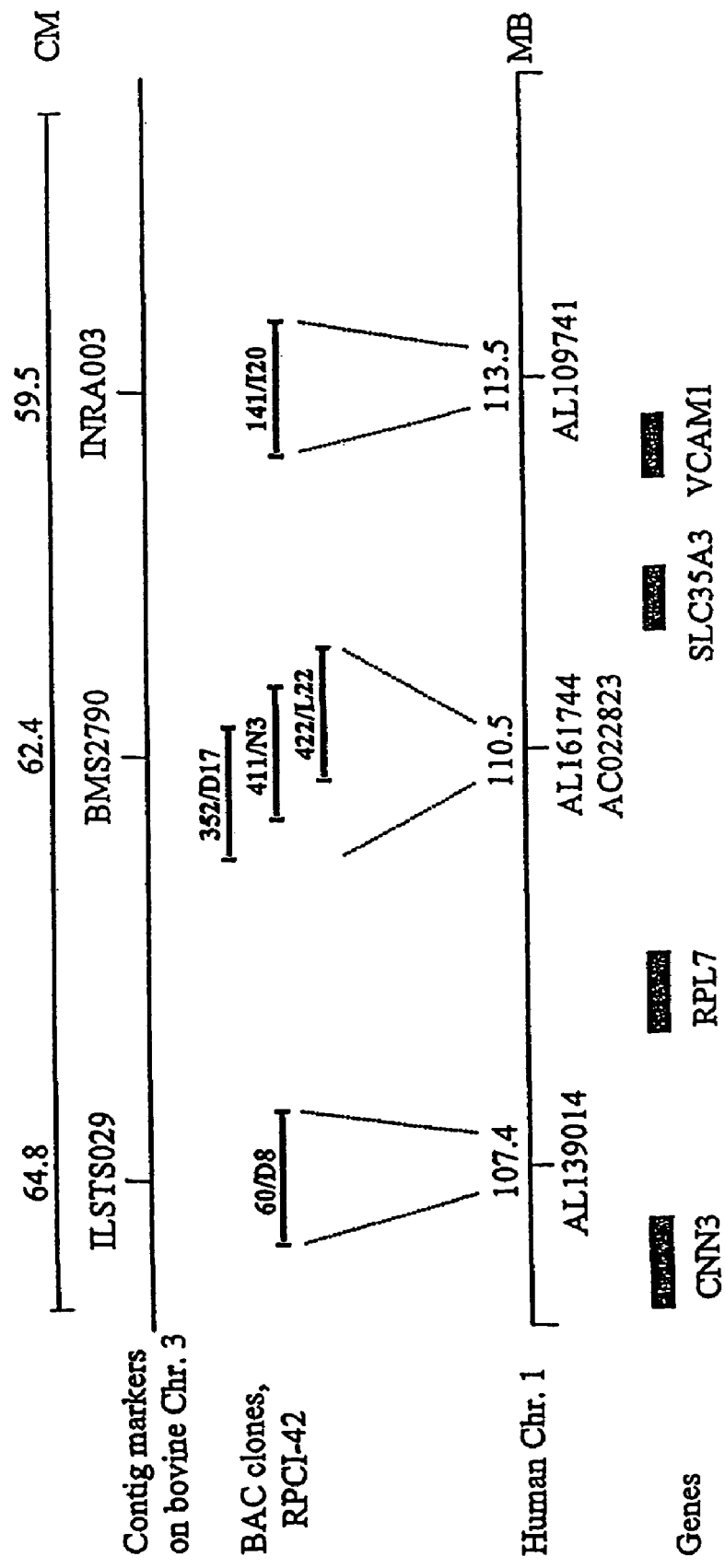

FIG. 3 shows the relative distance in cM between the 3 microsatellite markers ILSTS029, BMS2790 and INRA003 (shown on the line denoted Contig markers on bovine Chr. 3) on the bovine chromosome 3 as depicted by the U.S. Meat Animal Research Center (Kappes et al. 1997). BACs containing these 3 markers were isolated either by hybridisation to high density replica filters (ILSTS029 and INRA003), or by PCR screening of the RPCI-42 bovine BAC library (BMS2790). The identified BACs are shown in black bars and annotated by plate number/well number. These BACs were subjected to end-sequencing using SP6 and T7 primers or to sequencing using primers extending from the microsatellite. The resulting sequences were blasted against the human chromosome 1 using the Ensemble Server at the Sanger Centre. The accession numbers from the blast search are shown as numbers under the human chromosome 1 and the relative distance between the hits is given in MB. Selected genes in the region are shown in boxes.

FIG. 4 shows the cDNA sequence and translation of the SLC35A3 gene (SEQ ID NO: 18) and the encoded amino add sequence (SEQ ID NO: 17). The polymorphic nucleotide in position 559 and the affected valine-180 is indicated in bold.

FIG. 5 shows a comparison of the deduced amino add sequence of cow SLC35A3 with human (AB021981) (Ishida et al. 1999) and dog (AF057365) (Guillen et al. 1998) sequences. Dots indicate residues that match the Bos Taurus sequence. Dashes indicate gaps that have been introduced to optimise the alignment.

FIG. 6 shows the results obtained from sequencing the region (from nucleotide 544 to 572 of SLC35A3, see FIG. 4) showing the G/T polymorphism in position 559 in determination of CVM status by sequencing. The left and right panels show forward and reverse sequencing, respectively. The upper row (−/−) shows the sequencing of a wildtype animal, the middle row shows the sequencing of a carrier (heterozygote), and the lower row shows the sequencing of an affected animal.

FIG. 7 is a picture showing the Allele-Specific PCR products from two wildtype, two carriers, and two sick animals. Annotations: WT: wildtype, C: carrier, S: sick, neg: negative control, M: marker (size ladder). Arrows show the allele-specific PCR products: C: 220 bp, A: 98 bp, T: 340 bp, and G: 288 bp.

REFERENCES

1. Agerholm J S, Bendixen, C., Andersen O., Arnbjerg, J. (2000) LK meddelelser October 2000.
2. Barendse W, Valman D, Kemp S J, Sugimoto Y, Armitage S M, Williams J L, Sun H S, Eggen A, Agaba M, Aleyasin S A, Band M, Bishop M D, Bultkamp J, Byrne K, Collins F, Cooper L, Coppettiers W, Denys B, Drinkwater R D, Easterday K, Elduque C, Ennis S, Erhardt G, Li L, Lil L (1997) A medium-density genetic linkage map of the bovine genome. Mamm Genome 8, 21–28.
3. Brückner, K., Perez, L., Clausen, H., & Cohen, S., (2000) Glycosyltransferase activity of Fringe modulates Notch-Delta interactions *Nature* 406, pp. 411–415.
4. Evrad, Y. A., Lun, Y., Aulehla, A,. Gan, L, & Johnson, R. L. (1998) Lunatic fringe is an essential mediator of somite segmentation and patterning. *Nature* 394, pp. 377–381.
5. Guillen, E., Abeijon, C., & Hirschberg, C. B. (1998) Mammalian Golgi apparatus UDP-N-acetylglucosamine transporter: Molecular cloning by phenotypic correction of a yeast mutant. *Proc. Natl. Acad. Sci. USA*. 95, pp. 7888–7892.
6. Ishida, N., Yoshioka, S., Chiba, Y., Takeuchi, M., & Kawakita, M. (1999) Molecular cloning and functional expression of the human golgi UDP-N-acetylglucosamine transporter. *J. Biochem*. 126, pp. 68–77.
7. Kappes S M, Keele J W, Stone R T, McGraw R A, Sonstegard T S, Smith T P, Lopez-Corrales N L, Beattie C W (1997) A second-generation linkage map of the bovine genome. Genome Res 7, 235–249.
8. Klein, T., & Arias, M. (1998) Interactions among Delta, Serrate and Fringe modulate Notch activity during drosophila wing development. *Development* 125, pp. 2951–2962.
9. Lathrop G M, Lalouel J M, Julier C, Ott J (1985) Multilocus linkage analysis in humans: detection of linkage and estimation of recombination. Am J Hum Genet 37, 482–498
10. Moloney, D. J., Panin, V. M., Johnston, S. H., Chen, J., Shao, L, Wilson, Y., Stanley, P., Irvine, K. D., Haltiwanger, R. S., & Vogt, T. F. (2000) Fringe is a glycosyltransferase that modifies Notch. *Nature* 406, pp 369–375.
11. Solinas-Toldo S, Lengauer C, Fries R (1995) Comparative genome map of human and cattle Genomics 27, 489–496.

The invention claimed is:

1. A method for detecting bovine complex vertebral malformation (CVM) in a Holstein-Friesian subject said method comprising
   a) providing a Holstein-Friesian genetic material comprising a coding sequence which encodes either
      i) SEQ ID NO:17; or
      ii) a polypeptide which differs from SEQ ID NO:17 solely in that there is a phenylalanine at position 180, and
   b) detecting, in the Holstein-Friesian subject genetic material, the presence or absence of complex vertebral malformation disease, wherein the presence of a coding sequence encoding polypeptide ii) is indicative of CVM.

2. The a method according to claim 1, wherein the detection of the presence or absence of the coding sequence encoding polypeptide (ii) is performed by a technique selected from the group consisting of allele-specific PCR, minisequencing, primer-extension, pyro-sequencing, PCR-RFLP, allele-specific rolling circle amplification and primer-extension followed by MALDI-TOF mass-spectrometry.

* * * * *

UNITED STATES PATENT AND TRADEMARK OFFICE
CERTIFICATE OF CORRECTION

| | | |
|---|---|---|
| PATENT NO. | : 7,094,544 B2 | Page 1 of 1 |
| APPLICATION NO. | : 10/416941 | |
| DATED | : August 22, 2006 | |
| INVENTOR(S) | : Bendixen et al. | |

It is certified that error appears in the above-identified patent and that said Letters Patent is hereby corrected as shown below:

Title page item (75) Inventors, delete "Marck Jonker" and insert --Marc Jonker--.

Signed and Sealed this

Fourth Day of October, 2011

David J. Kappos
*Director of the United States Patent and Trademark Office*